United States Patent [19]
Murata et al.

[11] Patent Number: 5,500,221
[45] Date of Patent: Mar. 19, 1996

[54] SUSTAINED RELEASE SUPPOSITORY

[75] Inventors: Masami Murata, Narita; Harumi Kishi, Kashiwa; Takashi Narui, Sakura; Shuichi Kasai, Narita; Akira Iwasa, Yotsukaido, all of Japan

[73] Assignee: SS Pharmaceutical Co., Ltd., Tokyo, Japan

[21] Appl. No.: 215,970

[22] Filed: Mar. 18, 1994

Related U.S. Application Data

[63] Continuation of Ser. No. 946,435, filed as PCT/JP90/00666, May 24, 1990, abandoned.

[51] Int. Cl.$^6$ .............................. A61K 9/02; A61K 9/14; A61K 9/64
[52] U.S. Cl. .......................... 424/436; 424/451; 424/456; 424/489; 424/DIG. 15; 514/963; 514/966
[58] Field of Search ..................... 424/436, 456, 424/489, DIG. 15, 451; 514/966, 963

[56] References Cited

FOREIGN PATENT DOCUMENTS

| | | |
|---|---|---|
| 55-149209 | 11/1980 | Japan. |
| 56-138112 | 10/1981 | Japan. |
| 56-138110 | 10/1981 | Japan. |
| 0138111 | 10/1981 | Japan .............................. 424/DIG. 15 |
| 0138110 | 10/1981 | Japan .............................. 424/DIG. 15 |
| 0158719 | 9/1982 | Japan .............................. 424/DIG. 15 |
| 0038210 | 3/1983 | Japan .............................. 424/DIG. 15 |
| 0103326 | 6/1983 | Japan .............................. 424/DIG. 15 |
| 62-84018 | 4/1987 | Japan. |

*Primary Examiner*—Carlos A. Azpuru
*Attorney, Agent, or Firm*—Oblon, Spivak, McClelland, Maier & Neustadt

[57] ABSTRACT

The present invention relates to a sustained-release suppository preparation characterized by comprising an acidic drug or a salt thereof which can be absorbed by rectal administration and an acidic compound or a pH buffering agent. The sustained-release suppository preparation of the present invention exhibits no rapid increase in blood concentration immediately after the administration and maintains its action for a long period of time. Thus, it is safer and exhibits a better therapeutic effect.

9 Claims, 4 Drawing Sheets

SUSTAINED RELEASE SUPPOSITORY

This application is a Continuation of application Ser. No. 07/946,435, filed Nov. 18, 1992, abandoned, which was filed as International Application No. PCT/JP90/00666 on May 24, 1990.

FIELD OF THE INVENTION

The present invention relates to a sustained-release suppository preparation.

BACKGROUND ART

Suppository has a number of advantages. It not only can avoid decomposition of drugs by acid or enzyme in gastrointestinal tract when the drugs are orally administered or can avoid irritation stimulation to gastrointestinal mucosa which is caused by direct contact of drugs with mucosa, but also is physiologically less affected by such factors as variations of pH in gastrointestinal tract, the gastric empty rate, mobility of gastrointestinal tract, mutual actions between food components, and the like. In addition, suppository is safer and easier to administer than injection. Thus, it is a form of preparation which is applicable even to infant or elderly patients.

A number of incidents, however, have been reported on side effects of suppositories due to a rapid increase in blood concentration of drugs. On the other hand, drugs which are rapidly eliminated from blood must be administered more frequently in order to maintain their effect for a longer period of time. Administrating several times a day not only gives pain to the patients, but also is undesirable from the pharmacological aspect, e.g., irritation to mucosa, etc.

Development of a sustained-release suppository preparation which can avoid a rapid increase in blood concentration of drugs and exhibit its action for a longer period of time has therefore been desired.

In view of this situation, the present inventors have undertaken extensive studies and found that the release rate of acidic drugs or salts thereof, which can be absorbed by rectal administration and satisfactorily exhibit their effects, can be retarded if they are formulated together with an acidic compound or a pH buffering agent, thus controlling a rapid increase in blood concentration immediately after the administration and maintaining the blood concentration of the drug for a long period of time. This finding has led to the completion of the present invention.

DISCLOSURE OF THE INVENTION

The present invention provides a sustained-release suppository preparation characterized by comprising an acidic drug or a salt thereof which can be absorbed by rectal administration and an acidic compound or a pH buffering agent.

BEST MODE FOR CONDUCTING THE INVENTION

Figure 1:
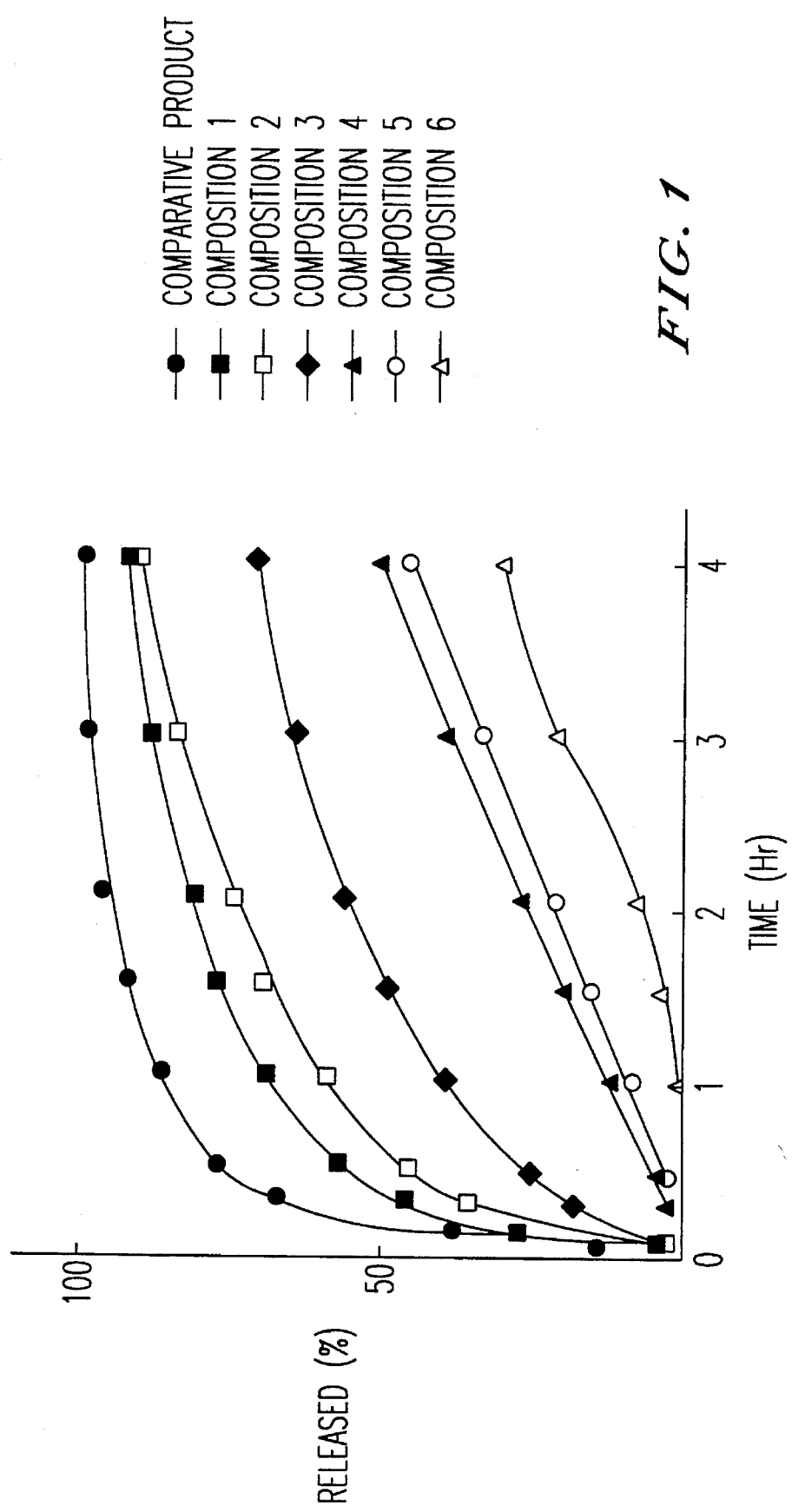
FIG. 1 is a drawing showing the result of the release test according to Test Example 1, wherein the relationship between the released percent of diclofenac sodium and time elapsed is shown.

There are no specific limitations as to acidic drugs or salts thereof used in the present invention so long as they can sufficiently be absorbed by rectal administration. Examples of such acidic drugs or salts thereof include flurazepam, nimetazepam, nitrazepam, perlapine, estazolam, haloxazolam, sodium valproate, sodium cromoglycate, primidone, alclofenac, perisoxal citrate, clidanac, indomethacin, sulpyrine, flufenamic acid, ketoprofen, sulindac, metiazinic acid, tolmetin sodium, fentiazac, naproxen, fenbufen, protizinic acid, pranoprofen, flurbiprofen, diclofenac sodium, mefenamic acid, ibuprofen, aspirin, dextran sulfate, carindacillin sodium, and the like.

There are also no specific limitations as to acidic compounds or pH buffering agents so long as they are capable of acidifying the site where the suppository is administered. Given as examples of acidic compounds are fumaric acid, tartaric acid, adipic acid, citric acid, malic acid, succinic acid, ascorbic acid, maleic acid, malonic acid, phosphoric acid, butyric acid, lactic acid, acetic acid, and the like. They can be used either singly or in their two or more combinations. As buffering agents, combinations with said acids and salts thereof can be used. As to the amount of these acidic compounds or pH buffering agents to be incorporated, an amount which can give the target sustained-release suppository is sufficient and such an amount varies depending on the characteristic of the drug used. Although there are no specific limitations, an amount of 0.02 part by weight or more per 1 part by weight of the acidic drug or a salt thereof is generally applicable.

Any base components commonly used for suppositories can be used as a base component of the suppository preparation of the present invention, including those derived from animal, vegetable or mineral origins, and materials partially or totally synthesized. Specific examples given of such base components include oils and fats of animals or vegetable origin, e.g., olive oil, corn oil, castor oil, cottonseed oil, wheat germ oil, cacao butter, hydrogenated oils, etc.; hydrocarbons, e.g., squalane, petrolatum, solid paraffin, liquid paraffin, etc.; and waxes, e.g., jojoba oil, carnauba wax, bees wax, lanolin, etc. As partially or totally synthesized fatty acid esters glycerol, mono-, di-, or triglycerides of medium or higher fatty acid, such as saturated linear fatty acid, e.g., lauric acid, myristic acid, palmitic acid, stearic acid, etc., or unsaturated linear fatty acid, e.g., oleic acid, linoleic acid, linolenic acid, etc, are given. Commercial products of these base components include Witepsol (manufactured by Dynamit Nobel), Pharmasol (manufactured by Nippon Oil and Fats Co.), Isocacao (manufactured by Kao Corp.), SB (manufactured by Taiyo Oil and Fats Co.), Novata (manufactured by Henkel), Suppocire (manufactured by Gattefosse Co.), and the like. Polyethylene glycol, e.g., macrogole, setomacrogole, etc., as well as derivatives thereof, e.g., setomacrogol, are given as examples of other synthetic products.

The sustained-release suppository preparations of the present invention, after the addition of an acidic drug or a salt thereof and an acidic compound or buffering agent to the base component, can be made in the form of solid suppositories, softgelation encapsule suppositories by soft gelatin or of rectal injection type ointments.

As needed, other additives such as absorption enhancers, preservatives, stabilizers, surfactants, perfumes, pigments, purified water, and the like may be added to the suppository preparation of the present invention. In addition, polymers, various types of carriers, gelling agents, and the like may be added in order to adjust the release rate of the drug.

There are no specific limitations as to the types of polymers so long as such polymers can be used for the purpose of adjusting the release rate of drugs. Specific examples include water insoluble polymers, e.g., ethylcellulose, aminoalkyl methacrylate copolymer, polyvinyl acetate, etc.; intestinally soluble polymers, e.g., cellulose acetate phthalate, hydroxypropylmethylcellulose phthalate, carboxymethylethylcellulose, stylene-acrylic acid copolymer, methacrylic acid copolymer, maleic acid anhydride copolymers, etc.; acid soluble polymers, e.g., polyvinylacetaldiethylamino acetate, aminoalkyl-methacrylate copolymer E, etc.; water-soluble polymers, e.g., hydroxypropylmethylcellulose, methylcellulose, hydroxypropylcellulose, polyvinylpyrrolidone, arginic acid, sodium arginate, acacia, agar, gelatin, polyamides, poly(lactic acid), poly(glycolic acid) copolymers, etc.; and the like. They may be used either singly or in their two or more combinations.

Polymers are used when a pharmaceutical composition comprising an acidic drug or a salt thereof is encapsulated into microcapsules or granulated. In this instance, the further addition of a carrier can help make the granulation process easier or adjust the rate of release of the drug. Examples of carriers include, but not limited to, organic compound powders such as fructose, glucose, lactose, sucrose, mannitol, starch, dextrin, α-starch, hydroxypropyl starch, microcrystalline cellulose, low-substituted hydroxypropyl cellulose, carboxymethyl cellulose, and the like, and inorganic compound powders such as light silicic anhydride, diatomaceous earth, magnesium silicate, aluminum silicate, calcium sulfate, calcium phosphate, precipitated calcium carbonate, talc, and the like.

For producing the sustained-release suppository preparation of the present invention in the form of microcapsule, microcapsules prepared from the drug composition comprising an acidic drug or a salt thereof by a conventional method are dispersed into a base component to which an acidic compound or a pH buffering agent is incorporated, or microcapsules prepared from the drug composition comprising an acidic drug or a salt thereof and an acidic compound or a pH buffering agent are dispersed into a suppository base component. For producing the sustained-release suppository preparation of the present invention in the form of granules, an acidic drug or a salt thereof and a polymeric compound are kneaded and granulated and the granules are dispersed into a base component to which an acidic compound or a pH buffering agent is incorporated, or an acidic drug or a salt thereof, an acidic compound or a pH buffering agent, and a polymeric compound are kneaded and granulated and the granules are dispersed into a suppository base component. In this instance, the polymeric compound may be used for kneading after dissolved in a suitable solvent or the polymers in a powdery form may be kneaded with a suitable solvent after mixing with other components.

Organic or inorganic gelling agents which can form a matrix in the base component or after the base component has melted or dissolved may be used as the gelling agent. Examples are pectin, chitin, chitosan, cross-linked polyacrylamide, polyacrylic acid, arginic acid, sodium arginate, gelatin, agar, acacia, xanthane gum, guar-gum, carboxyvinyl polymer, polyvinyl alcohol, methylcellulose, hydroxypropylmethylcellulose, hydroxypropylcellulose, aminoalkylmethacrylate copolymer, light silicic anhydride, aluminum hydroxide, magnesium hydroxide, and the like.

It is possible to incorporate two or more layers, each having a different release rate of drugs, into a suppository preparation, thus enabling the release rate at absorption sites to be controlled. This can be achieved by a method preparing the sustained-release suppository preparation by dispersing or dissolving a portion of said acidic drug in the base component and adding said microcapsules or granules to the solution or the dispersion, a method of preparing the sustained-release suppository preparation as a multi-layered suppository having two or more layers with different release rates, or a method of preparing the sustained-release suppository preparation as a suppository having a core and two or more layers with different release rates.

EXAMPLES

The present invention is illustrated by way of examples of suppositories in which non-steroidal anti-inflammatory drugs are used, among suppositories for local or systemic administration. These examples are not intended to be limiting of the present invention.

EXAMPLE 1

Diclofenac sodium and fumaric acid were suspended in molten Witepsol H5 (a product of Dynamit Nobel) and processed according to a conventional method to obtain sustained-release suppository preparations having compositions shown in Table 1.

TABLE 1

| | Composition | | | | | (Unit: mg) |
|---|---|---|---|---|---|---|
| Component | 1 | 2 | 3 | 4 | 5 | 6 |
| Diclofenac sodium | 25 | 25 | 25 | 25 | 25 | 25 |
| Fumaric acid | 0.5 | 10 | 20 | 40 | 80 | 160 |
| Witepsol H5 | 974.5 | 965 | 955 | 935 | 895 | 815 |
| Total | 1000 | 1000 | 1000 | 1000 | 1000 | 1000 |

EXAMPLE 2

Diclofenac sodium and tartaric acid were suspended in molten Witepsol H5 and poured into containers to obtain sustained-release suppositories, each weighing 1 g.

| | |
|---|---|
| Diclofenac sodium | 2.5 g |

| | |
|---|---|
| Tartaric acid | 16.0 g |
| Witepsol H5 | 81.5 g |
| Total | 100.0 g |

EXAMPLE 3

Diclofenac sodium and ascorbic acid were suspended in molten Witepsol H5 and poured into containers to obtain sustained-release suppositories, each weighing 1 g.

| | |
|---|---|
| Diclofenac sodium | 2.5 g |
| Ascorbic acid | 16.0 g |
| Witepsol H5 | 81.5 g |
| Total | 100.0 g |

EXAMPLE 4

Indomethacin and fumaric acid were suspended in molten Witepsol H5 and poured into containers to obtain sustained-release suppositories, each weighing 1 g.

| | |
|---|---|
| Indomethacin | 2.5 g |
| Fumaric acid | 16.0 g |
| Witepsol H5 | 81.5 g |
| Total | 100.0 g |

EXAMPLE 5

Ketoprofen and fumaric acid were suspended in molten Witepsol H5 and poured into containers to obtain sustained-release suppositories, each weighing 1 g.

| | |
|---|---|
| Ketoprofen | 2.5 g |
| Fumaric acid | 16.0 g |
| Witepsol H5 | 81.5 g |
| Total | 100.0 g |

EXAMPLE 6

Diclofenac sodium and sodium dihydrogenphosphate were suspended in molten Witepsol H5 and poured into containers to obtain sustained-release suppositories, each weighing 1 g.

| | |
|---|---|
| Diclofenac sodium | 2.5 g |
| Sodium dihydrogenphosphate | 16.0 g |
| Witepsol H5 | 81.5 g |
| Total | 100.0 g |

EXAMPLE 7

Mefenamic acid and adipic acid were suspended in molten Polyethylene glycol 1540 (manufactured by Nippon Oil and Fats Co.) and poured into containers to obtain sustained-release suppositories, each weighing 1 g.

| | |
|---|---|
| Mefenamic acid | 25.0 g |
| Adipic acid | 16.0 g |
| Polyethylene glycol 1540 | 59.0 g |
| Total | 100.0 g |

EXAMPLE 8

Metiazinic acid and citric acid were suspended in molten Isocacao MH-35 (manufactured by Kao Corp.) and poured into containers to obtain sustained-release suppositories, each weighing 1 g.

| | |
|---|---|
| Metiazinic acid | 25.0 g |
| Citric acid | 16.0 g |
| Isocacao MH-35 | 59.0 g |
| Total | 100.0 g |

EXAMPLE 9

Disodium cromoglycate and tartaric acid were suspended in molten cacao butter and filled into containers to obtain sustained-release suppositories, each weighing 1 g.

| | |
|---|---|
| Disodium cromoglycate | 2.5 g |
| Tartaric acid | 16.0 g |
| Cacao butter | 81.5 g |
| Total | 100.0 g |

EXAMPLE 10

Diclofenac sodium and fumaric acid were suspended into macrogole (400) and encapsulated into soft capsules to obtain sustained-release suppositories, each weighing 1 g.

| | |
|---|---|
| Contents: | |
| Diclofenac sodium | 2.5 g |
| Fumaric acid | 16.0 g |
| Macrogole 400 | 41.5 g |
| Total | 60.0 g |
| Capsules: | |
| Gelatin | 28.0 g |
| Glycerol | 7.96 g |
| Ethyl p-oxybenzoate | 0.04 g |
| Purified water | 4.0 g |
| Total | 40.0 g |

EXAMPLE 11

Microcapsules were prepared from a mixture of diclofenac sodium and fumaric acid by a solvent evaporation method. The microcapsules were suspended in Witepsol H5 and poured into containers to obtain sustained-release suppositories, each weighing 1 g.

| Microcapsules: | |
| --- | --- |
| Diclofenac sodium | 2.5 g |
| Fumaric acid | 1.0 g |
| Aminoalkyl methacrylate copolymer | 1.0 g |
| Magnesium stearate | 0.5 g |
| Total | 5.0 g |
| Microcapsules (Containing 50% of diclofenac sodium) | 5.0 g |
| Witepsol H5 | 95.0 g |
| Total | 100.0 g |

EXAMPLE 12

Microcapsules were prepared from a mixture of diclofenac sodium and fumaric acid by a solvent evaporation method. The microcapsules were suspended in molten Pharmasol B-105 (manufactured by Nippon Oil and Fats Co.) and poured into containers to obtain sustained-release suppositories, each weighing 1 g.

| Microcapsules: | |
| --- | --- |
| Diclofenac sodium | 2.5 g |
| Fumaric acid | 1.0 g |
| Hydroxypropylcellulose | 1.0 g |
| Magnesium stearate | 0.5 g |
| Total | 5.0 g |
| Microcapsules (Containing 50% of diclofenac sodium) | 5.0 g |
| Pharmasol B-105 | 95.0 g |
| Total | 100.0 g |

EXAMPLE 13

Diclofenac sodium, sodium arginate, and fumaric acid were suspended in molten Witepsol H5 and poured into containers to obtain sustained-release suppositories, each weighing 1 g.

| Diclofenac sodium | 2.5 g |
| --- | --- |
| Fumaric acid | 2.5 g |
| Sodium arginate | 20.0 g |
| Witepsol H5 | 75.0 g |
| Total | 100.0 g |

EXAMPLE 14

Diclolofenac sodium and light silicic anhydride were kneaded with a solution of methacrylic acid copolymer L in ethanol, dried and pulverized to obtain granules. The granules and fumaric acid were suspended in molten Witepsol H15 and poured into containers to obtain sustained-release suppositories, each weighing 1.8 g.

| Diclofenac sodium | 5.0 g |
| --- | --- |
| Fumaric acid | 8.0 g |
| Light silicic anhydride | 25.5 g |
| Methacrylic acid copolymer L | 5.0 g |
| Witepsol H15 | 136.5 g |
| Total | 180.0 g |

EXAMPLE 15

Diclofenac sodium and light silicic anhydride were kneaded with a solution of polyvinylpyrrolidone in ethanol, dried and pulverized to obtain granules. The granules and fumaric acid were suspended in molten Witepsol H15 and poured into containers to obtain sustained-release suppositories, each weighing 1.8 g.

| Diclofenac sodium | 5.0 g |
| --- | --- |
| Fumaric acid | 8.0 g |
| Light silicic anhydride | 25.5 g |
| Polyvinylpyrrolidone | 5.0 g |
| Witepsol H15 | 136.5 g |
| Total | 180.0 g |

EXAMPLE 16

Diclofenac sodium and light silicic anhydride were kneaded with a solution of methacrylic acid copolymer S in ethanol, dried and pulverized to obtain granules. The granules and fumaric acid were suspended in molten Witepsol H15 and poured into containers to obtain sustained-release suppositories, each weighing 1.8 g.

| Diclofenac sodium | 5.0 g |
| --- | --- |
| Fumaric acid | 8.0 g |
| Light silicic anhydride | 25.5 g |
| Methacrylic acid copolymer S | 5.0 g |
| Witepsol H15 | 136.5 g |
| Total | 180.0 g |

EXAMPLE 17

Diclofenac sodium and light silicic anhydride were kneaded with a solution of hydroxypropylmethylcellulose in ethanol, dried and pulverized to obtain granules. The granules and fumaric acid were suspended in molten Witepsol H15 and poured into containers to obtain sustained-release suppositories, each weighing 1.8 g.

| Diclofenac sodium | 5.0 g |
| --- | --- |
| Fumaric acid | 8.0 g |
| Light silicic anhydride | 25.5 g |
| Hydroxypropylmethylcellulose | 5.0 g |
| Witepsol H15 | 136.5 g |
| Total | 180.0 g |

EXAMPLE 18

Diclofenac sodium and light silicic anhydride were kneaded with a solution of ethylcellulose in ethanol, dried and pulverized to obtain granules. The granules and fumaric acid were suspended in molten Witepsol H15 and poured into containers to obtain sustained-release suppositories, each weighing 1.8 g.

| | |
|---|---|
| Diclofenac sodium | 5.0 g |
| Fumaric acid | 8.0 g |
| Light silicic anhydride | 25.5 g |
| Ethylcellulose | 5.0 g |
| Witepsol H15 | 136.5 g |
| Total | 180.0 g |

EXAMPLE 19

Diclofenac sodium and methacrylic acid copolymer L were kneaded with ethanol, dried and pulverized to obtain granules. The granules and fumaric acid were suspended in molten Witepsol H15 and poured into containers to obtain sustained-release suppositories, each weighing 1.8 g.

| | |
|---|---|
| Diclofenac sodium | 5.0 g |
| Fumaric acid | 8.0 g |
| Methacrylic acid copolymer L | 5.0 g |
| Witepsol H15 | 162.0 g |
| Total | 180.0 g |

EXAMPLE 20

Diclofenac sodium and light silicic anhydride were kneaded with a solution of methacrylic acid copolymer L in ethanol, dried and pulverized to obtain granules. The granules and fumaric acid were suspended in molten Witepsol H15 and poured into containers to obtain sustained-release suppositories, each weighing 1.8 g.

| | |
|---|---|
| Diclofenac sodium | 5.0 g |
| Fumaric acid | 8.0 g |
| Light silicic anhydride | 25.5 g |
| Methacrylic acid copolymer L | 5.0 g |
| Witepsol H15 | 136.5 g |
| Total | 180.0 g |

EXAMPLE 21

Diclofenac sodium, light silicic anhydride, and fumaric acid were kneaded with a solution of methacrylic acid copolymer L in ethanol, dried and pulverized to obtain granules. The granules were suspended in molten Witepsol H15 and poured into containers to obtain sustained-release suppositories, each weighing 1.8 g.

| | |
|---|---|
| Diclofenac sodium | 5.0 g |
| Fumaric acid | 8.0 g |
| Light silicic anhydride | 25.5 g |
| Methacrylic acid copolymer L | 5.0 g |
| Witepsol H15 | 136.5 g |
| Total | 180.0 g |

COMPARATIVE EXAMPLE 1

Diclofenac sodium was suspended in molten Witepsol H5 and poured into containers to obtain suppositories, each weighing 1 g.

| | |
|---|---|
| Diclofenac sodium | 2.5 g |
| Witepsol H5 | 97.5 g |
| Total | 100.0 g |

COMPARATIVE EXAMPLE 2

Indomethacin was suspended in molten Witepsol H5 and poured into containers to obtain suppositories, each weighing 1 g.

| | |
|---|---|
| Indomethacin | 2.5 g |
| Witepsol H5 | 97.5 g |
| Total | 100.0 g |

COMPARATIVE EXAMPLE 3

Ketoprofen was suspended in molten Witepsol H5 and poured into containers to obtain suppositories, each weighing 1 g.

| | |
|---|---|
| Ketoprofen | 2.5 g |
| Witepsol H5 | 97.5 g |
| Total | 100.0 g |

COMPARATIVE EXAMPLE 4

Diclofenac sodium was suspended in molten Witepsol H15 and poured into containers to obtain suppositories, each weighing 1.8 g.

| | |
|---|---|
| Diclofenac sodium | 5.0 g |
| Witepsol H15 | 75.0 g |
| Total | 180.0 g |

TEST EXAMPLE1

Release tests of active components from the sustained-release suppository prepared in Example 1 and the suppository prepared in Comparative Example 1 were carried out by using a suppository dissolution tester (TMS-103) manufactured by Toyama Sangyo Co., Ltd., Osaka, Japan. A phosphate buffer solution prepared by diluting a pH 7.2 phosphate buffer, defined in the chapter of reagents and solutions in the Pharmacopoeia of Japan (11th Edition), to a volume of 10 times (37° C.) was used as a receptor solution. The donor charge cell and the receptor phase were partitioned by an artificial membrane (millipore filter) having 0.8 μm pores. Compartments for the receptor and the receptor phase were stirred at a rate of 25 rpm and 100 rpm, respectively. The results are shown in FIG. 1.

As clear from FIG. 1, the suppository of Example 1 containing fumaric acid in an amount of 0.02 part by weight or more of the active component manifestly exhibited controlled release as compared with the suppository of Comparative Example 1 which contained no fumaric acid.

TEST EXAMPLE 2

Release tests of active components from the sustained-release suppositories prepared in Examples 2, 3, and 13 were carried out in the same manner as in Test Example 1. The results are shown in FIG. 2.

Figure 2:
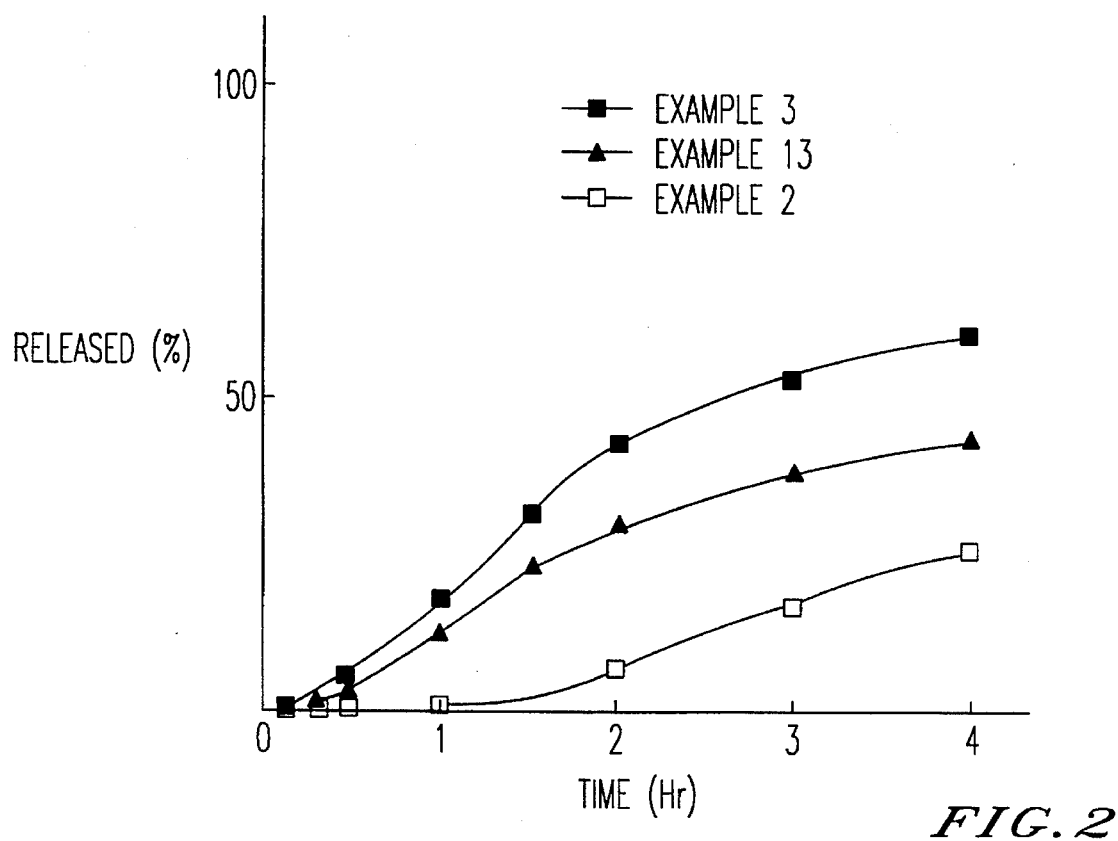
FIG. 2 is a drawing showing the result of the release test according to Test Example 2, wherein the relationship between the released percent of diclofenac sodium and the time elapsed is shown.

As clear from FIG. 2, the release of diclofenac sodium was controlled in all Examples 2, 3, and 13.

TEST EXAMPLE 3

Release tests of active components from the sustained-release suppositories prepared in Examples 4 and 5 and suppositories prepared in Comparative Examples 2 and 3 were carried out in the same manner as in Test Example 1. The results are shown in FIG. 3.

Figure 3:
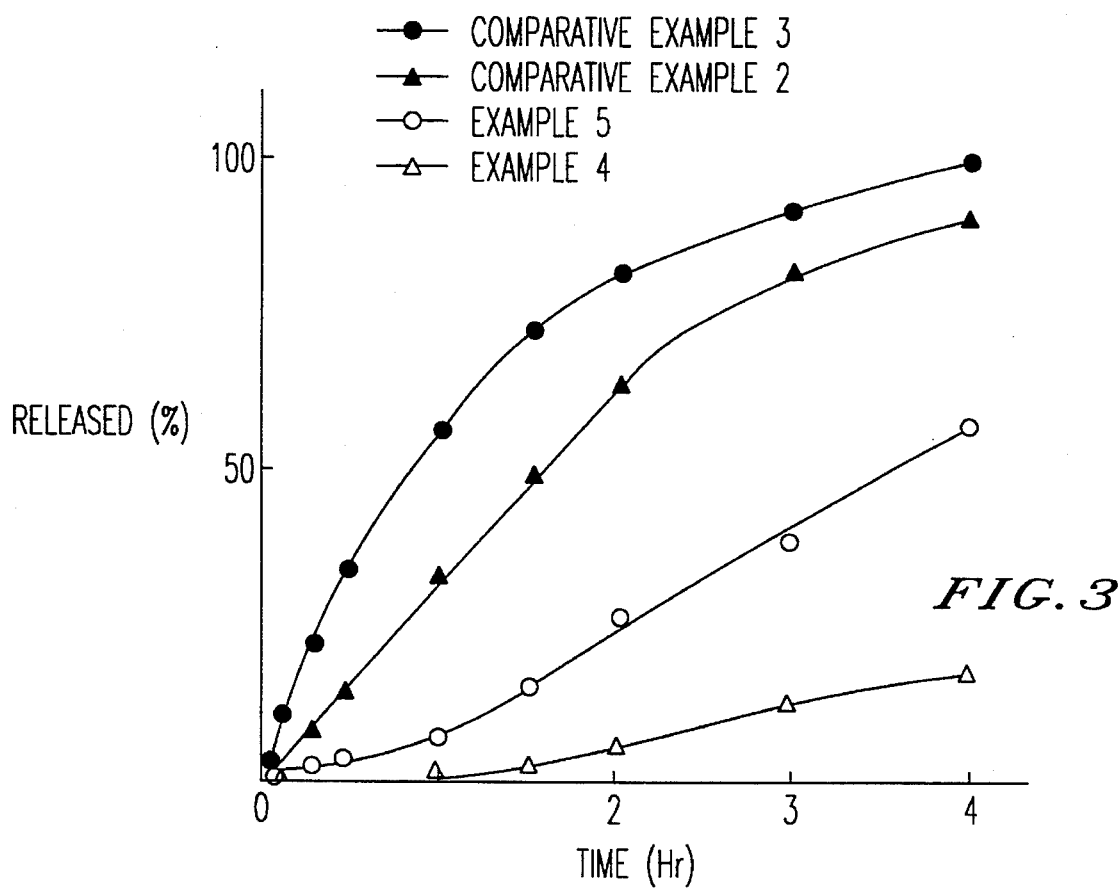
FIG. 3 is a drawing showing the result of the release test according to Test Example 3, wherein the relationship between the released percent of the active component and the time elapsed is shown.

As clear from FIG. 3, the suppositories of both Examples 4 and 5 containing fumaric acid exhibited more controlled release of the active component than the suppositories of Comparative Examples 2 and 3 which contained no fumaric acid.

TEST EXAMPLE 4

The sustained-release suppositories prepared in Example 1 (Compositions 4–6), the sustained-release suppository prepared in Example 2, and the suppository prepared in Comparative Example 1 were administered to male rabbits, weighing 2–2.5 kg. After the administration, blood samples were collected at predetermined time. Plasma diclofenac sodium concentrations were determined by high performance liquid chromatography. The results are shown in FIG. 4.

Figure 4:
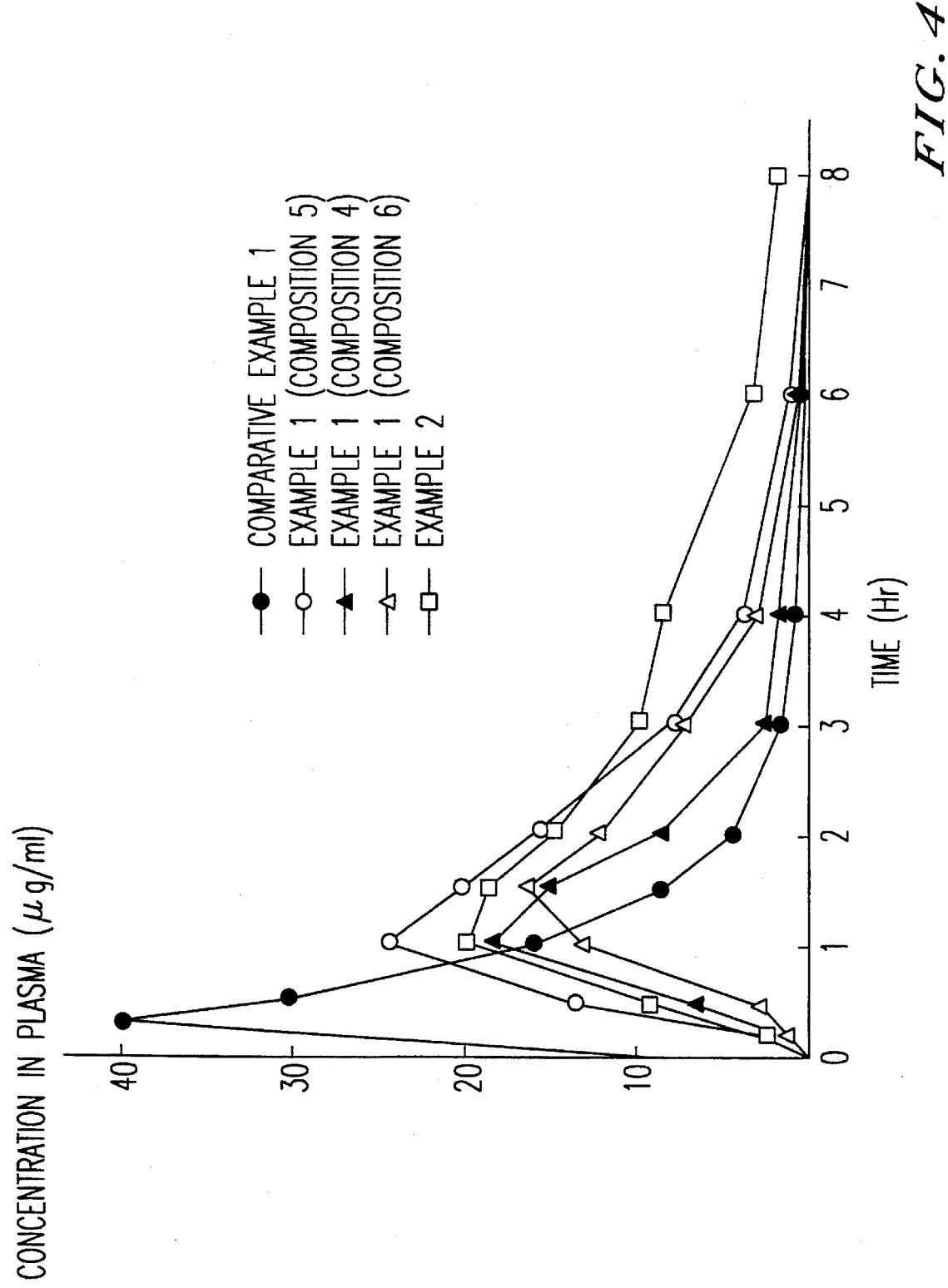
FIG. 4 is a drawing showing the relationship between the concentration of diclofenac sodium in plasma and the time after the administration to rabbits according to Test Example 4.

As clearly shown in FIG. 4, suppositories of the present invention containing fumaric acid or tartaric acid all exhibited no rapid increase nor rapid decrease in blood concentration.

TEST EXAMPLE 5

The release tests of active components were carried out in the same manner as in Test Example 1 and the blood concentration measurement tests were carried out in the same manner as in Test Example 4 on the sustained-release suppository prepared in Example 14 and the suppository prepared in Comparative Example 4. The results are shown in FIGS. 5 and 6, respectively.

Figure 5:
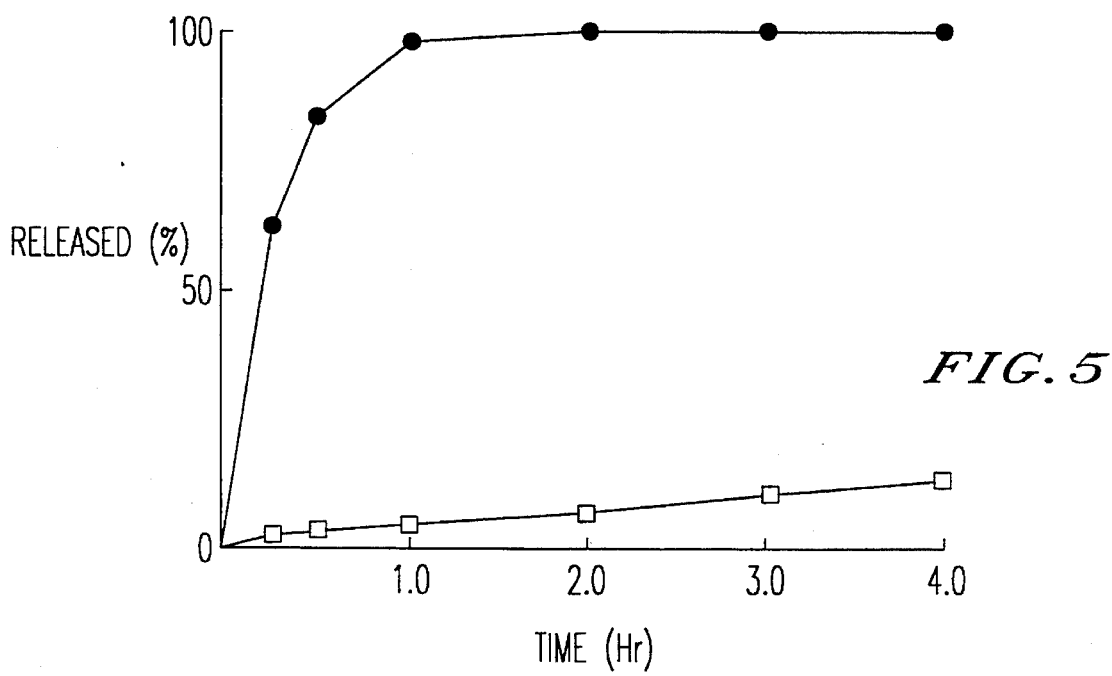
FIG. 5 is a drawing showing the result of the release test according to Test Example 5, wherein the relationship between the released percent of diclofenac sodium and the time elapsed is shown.
Figure 6:
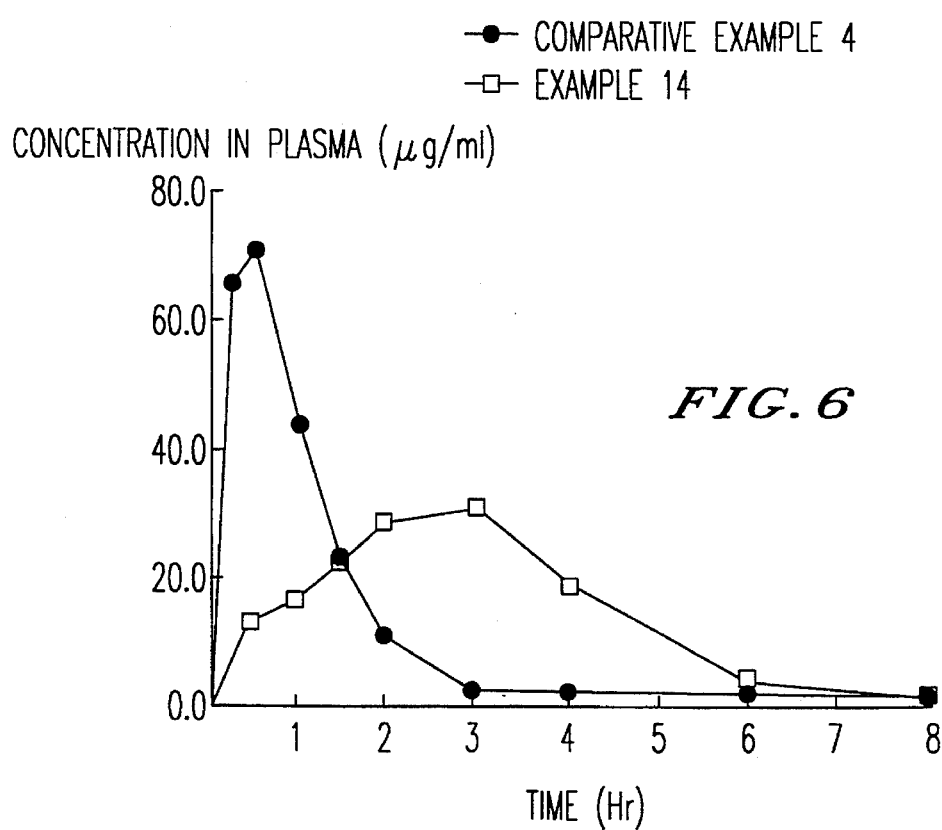
FIG. 6 is a drawing showing the relationship between the concentration of diclofenac sodium in plasma and the time elapsed after the administration to rabbits according to Test Example 5.

As clearly shown in FIGS. 5 and 6, the suppositories of the present invention exhibited well-controlled release of the active component, showed neither a rapid increase nor rapid decrease in the blood concentration.

INDUSTRIAL APPLICABILITY

The sustained-release suppository preparation of the present invention can control the release of acidic drugs or salts thereof contained therein to the sites where they are absorbed. As a result, their effective blood concentration can be maintained without a rapid increase, thus ensuring remarkable promotion of the therapeutic effects by the drugs.

The generic names of the following drug tradenames are provided hereinbelow for convenience:

Naproxen: (S)-6-methoxy-α-methyl-2-naphthyleneacetic acid,

Fenbufen: γ-oxo-(1,1'-biphenyl)-4-butanoic acid,

Pranoprofen: α-methyl-5H-(1) benzopyrino(2,3-b) pyridine- 7-acetic acid,

Flurbiprofen: 2-fluoro-α-methyl(1,1'-biphenyl)-4-acetic acid,

Ibuprofen: α-methyl-4-(2-methylpropyl)benzeneacetic acid, and

Aspirin: 2-(acetyloxy)benzoic acid.

We claim:

1. A sustained-release suppository preparation, comprising a therapeutically effective amount of an acidic drug or a pharmaceutically acceptable salt thereof which can be absorbed by rectal administration and an acidic compound or a pH buffering agent mixed in a pharmaceutically acceptable base component, wherein said acidic drug or pharmaceutically acceptable salt thereof is selected from the group consisting of sodium valproate, sodium cromoglycate, alclofenac, clidanac, indomethacin, sulpyrin, flufenamic acid, ketoprofen, sulindac, metiazinic acid, tolmetin sodium, fentiazac, (S)-6-methoxy-α-methyl-2-naphthyleneacetic acid, γ-oxo-(1,1'-biphenyl)-4-butanoic acid, protizinic acid, α-methyl- 5H-(1)benzopyrino(2,3-b)pyridine-7-acetic acid, 2-fluoro-α-methyl( 1,1'-biphenyl)-4-acetic acid, diclofenac sodium, mefenamic acid, α-methyl-4-(2-methylpropyl) benzeneacetic acid and 2-(acetyloxy)benzoic acid.

2. The sustained-release suppository preparation according to claim 1, wherein said acidic compound is selected from the group consisting of fumaric acid, tartaric acid, adipic acid, citric acid, malic acid, succinic acid, ascorbic acid, maleic acid, malonic acid, phosphoric acid, butyric acid, lactic acid and acetic acid.

3. The sustained-release suppository preparation according to claim 1, containing 0.02 parts by weight of said acidic compound or pH buffering agent for 1 part by weight of said acidic drug or pharmaceutically acceptable a salt thereof.

4. The sustained-release suppository preparation according to claim 1, further comprising a pharmaceutically acceptable polymer.

5. The sustained-release suppository preparation according to claim 1, further comprising a pharmaceutically acceptable polymer and a pharmaceutically-acceptable carrier.

6. The sustained-release suppository preparation according to claim 1, wherein said acidic drug or pharmaceutically acceptable salt thereof or said acidic compound or pH buffering agent dispersed in said pharmaceutically acceptable base component are in a form of microcapsules or granules.

7. The sustained-release suppository preparation according to claim 6, wherein said microcapsules or granules comprising said acidic drug or pharmaceutically acceptable salt thereof are dispersed in a pharmaceutically acceptable base component wherein said acidic compound or pH buffering agent is dispersed or dissolved.

8. The sustained-release suppository preparation according to claim 1, comprising an organic or inorganic gelling agent which can form a matrix in said pharmaceutically acceptable base component or after said pharmaceutically acceptable base component is melted or dissolved.

9. The sustained-release suppository preparation according to claim 1, wherein two or more layers having different release rates are incorporated.

* * * * *